(12) United States Patent
Kraus et al.

(10) Patent No.: US 9,962,263 B2
(45) Date of Patent: May 8, 2018

(54) ELECTRIC HIP JOINT PROSTHESIS

(75) Inventors: Werner Kraus, Munich (DE);
Stephanie Kraus, Munich (DE);
Heribert Stephan, Munich (DE); Peter Willsau, legal representative, Munich (DE)

(73) Assignee: Neue Magnetodyn GmbH, Munich (DE)

( * ) Notice: Subject to any disclaimer, the term of this patent is extended or adjusted under 35 U.S.C. 154(b) by 0 days. days.

(21) Appl. No.: 13/147,715

(22) PCT Filed: Jan. 26, 2010

(86) PCT No.: PCT/EP2010/000456
§ 371 (c)(1),
(2), (4) Date: Nov. 1, 2011

(87) PCT Pub. No.: WO2010/089044
PCT Pub. Date: Aug. 12, 2010

(65) Prior Publication Data
US 2012/0041565 A1  Feb. 16, 2012

(30) Foreign Application Priority Data
Feb. 3, 2009 (DE) .................. 10 2009 007 195

(51) Int. Cl.
*A61F 2/32* (2006.01)
*A61F 2/36* (2006.01)
(Continued)

(52) U.S. Cl.
CPC .......... *A61F 2/367* (2013.01); *A61F 2/30744* (2013.01); *A61F 2002/2821* (2013.01);
(Continued)

(58) Field of Classification Search
CPC .................. A61F 2002/2821; A61F 2/367
(Continued)

(56) References Cited

U.S. PATENT DOCUMENTS

| 4,195,367 | A | * | 4/1980 | Kraus | .................. | A61B 17/58 |
| | | | | | | 433/173 |
| 4,214,322 | A | | 7/1980 | Kraus | | |

(Continued)

FOREIGN PATENT DOCUMENTS

| DE | 2 315 517 A1 | 10/1973 |
| DE | 26 11 744 A1 | 9/1977 |

(Continued)

OTHER PUBLICATIONS

German Office Action dated Oct. 2, 2009 with English translation (ten (10) pages).

(Continued)

*Primary Examiner* — Bruce E Snow
*Assistant Examiner* — Melissa Hoban
(74) *Attorney, Agent, or Firm* — Crowell & Moring LLP

(57) ABSTRACT

The invention relates to a hip joint prosthesis comprising a shaft-like section that can be inserted into a femur, and a proximally arranged end cap assembly which closes a hollow space of the hip joint prosthesis. According to the invention the end cap assembly carries a coil assembly that is connected to a first electrode with a first pole and to a second electrode with a second pole. The first and the second electrodes enclose surfaces of the hip joint prosthesis, and in a state in which the end cap assembly closes the hollow space of the hip joint prosthesis, the coil assembly is predominantly arranged in the hollow space.

18 Claims, 2 Drawing Sheets

(51) Int. Cl.
*A61F 2/30* (2006.01)
*A61F 2/28* (2006.01)
*A61F 2/48* (2006.01)

(52) U.S. Cl.
CPC ............. *A61F 2002/3067* (2013.01); *A61F 2002/3068* (2013.01); *A61F 2002/30332* (2013.01); *A61F 2002/30507* (2013.01); *A61F 2002/30668* (2013.01); *A61F 2002/30677* (2013.01); *A61F 2002/368* (2013.01); *A61F 2002/482* (2013.01); *A61F 2220/0025* (2013.01); *A61F 2220/0033* (2013.01); *A61F 2250/0001* (2013.01); *A61F 2250/0002* (2013.01); *A61F 2250/0068* (2013.01); *A61F 2310/00239* (2013.01)

(58) Field of Classification Search
USPC ................ 623/22.42, 23.16, 23.18, 23.49
See application file for complete search history.

(56) References Cited

U.S. PATENT DOCUMENTS

| | | | |
|---|---|---|---|
| 4,216,548 A | | 8/1980 | Kraus |
| 5,030,236 A | * | 7/1991 | Dean ................. A61F 2/367 433/201.1 |
| 5,645,740 A | * | 7/1997 | Naiman et al. .......... 219/121.68 |
| 6,034,295 A | | 3/2000 | Rehberg et al. |
| 6,126,691 A | * | 10/2000 | Kasra ................ A61F 2/3662 606/63 |
| 6,778,861 B1 | | 8/2004 | Liebrecht et al. |
| 2003/0040806 A1 | * | 2/2003 | MacDonald ............. 623/23.49 |
| 2004/0180072 A1 | | 9/2004 | Tunc et al. |
| 2005/0012610 A1 | * | 1/2005 | Liao .................... A61B 5/0008 340/539.12 |
| 2005/0137711 A1 | * | 6/2005 | Southworth et al. ...... 623/22.46 |
| 2005/0256586 A1 | | 11/2005 | Kraus et al. |
| 2005/0288794 A1 | * | 12/2005 | Khalili et al. .............. 623/22.41 |
| 2006/0004431 A1 | * | 1/2006 | Fuller .................. A61B 17/86 607/116 |
| 2006/0052877 A9 | * | 3/2006 | Doubler et al. ........... 623/22.42 |
| 2006/0093646 A1 | | 5/2006 | Cima et al. |
| 2006/0265026 A1 | * | 11/2006 | Madjar ................ A61C 8/0006 607/51 |
| 2010/0036467 A1 | * | 2/2010 | Kraus ..................... A61N 1/05 607/116 |
| 2010/0063499 A1 | * | 3/2010 | Pein ..................... A61F 2/4603 606/41 |

FOREIGN PATENT DOCUMENTS

| | | |
|---|---|---|
| DE | 37 09 734 A1 | 10/1988 |
| DE | 295 06 036.0 U1 | 6/1995 |
| DE | 44 21 154 A1 | 12/1995 |
| DE | 195 44 750 A1 | 6/1997 |
| DE | 199 28 449 C1 | 3/2001 |
| DE | 10 2004 024 473 A1 | 12/2005 |
| EP | 0 781 532 A2 | 7/1997 |
| WO | WO 2008/035089 A1 | 3/2008 |

OTHER PUBLICATIONS

International Search Report dated Jun. 11, 2010 with English translation (six (6) pages).

* cited by examiner

ELECTRIC HIP JOINT PROSTHESIS

BACKGROUND AND SUMMARY OF THE INVENTION

The invention relates to a hip joint prosthesis comprising a shaft-like section insertable into a femur and a proximally arranged end cap assembly closing the a hollow space of the hip joint prosthesis.

Such hip joint prostheses are known in the field of endoprosthetics, for example, from DE 295 06 036 U1.

Problematic with such inelastic, tissue-replacing implants is, however, the interference with biological recovery, primarily due to the loss of blood vessels and nerves. In addition, the biomechanical quality of the support structure will suffer with increasing implantation time due to the partial elimination of its function. With the loss of biological control, however, the risk of infection by drug-resistant bacteria (MRSA=multi-resistant staphylococcus aureus) will increase. It has been shown that these bacteria may colonise the surface of metal implants in the form of an adherent bio film and resist attack from antibiotics with the aid of a mucous layer of polysaccharides.

Within the framework of orthopedic surgery, these problems can be addressed by magnetically induced electro-osteotherapy. Examples are known from DE 10 2004 024 473 A1 and DE 199 28 449 A1. In electro-osteotherapy, electric alternating potentials with a low frequency are induced in endoprostheses or osteosythesis means by subjecting an affected part of the body to an alternating magnetic field. It has long been demonstrated in numerous clinical applications of the technology according to the method to chronically therapy-resistant, in most cases, infected bone defects, cysts and tumor metastases, as well as in clinic-oriented experimental studies that an optimum healing effect can be obtained by using implants as sources of extremely low-frequency sinusoidal electric alternating potentials in the bone region adjacent to the implant.

The transmission technique functions according to the transformer principle: the injured or ill body region is flooded by an extremely low-frequency sinusoidally extending magnetic field having a frequency of approximately 1 to 100 Hz—preferably of 4 to 20 Hz—and a magnetic flux density of 0.5 to 5 mT (5 to 50 Gauss) which is generated by a function generator in one or more—primary—outer current coils into which the body part provided with the implant is introduced. These extremely low-frequency electromagnetic fields permeate the tissue including any clothing and/or casts, as well as non-magnetic (austenitic) implant metals largely without loss. A—secondary—coil assembly, which is often referred to as a transformer, is implanted in electric contact with these. The electric potentials induced in the transformer are thus brought into effect in the tissue adjacent to the implant.

With this technology of inductively transmitting therapeutically effective electric potentials to the components of the implant, the infection risk posed by percutaneous power supply lines is avoided, and the treatment parameters of electric voltage, frequency, intensity, signal form, and treatment time can be determined by the indication-specific programming of a function generator of the induced magnetic field.

The object of the invention is to improve an orthopedic implant in the form of a generic hip joint prosthesis particularly with respect to its manageability and flexible usability during the operation, its biological effect, its therapeutic effectivity and its efficiency.

The invention is based on the generic hip joint prosthesis in that the end cap assembly carries a coil assembly connected to a first electrode with a first pole and to a second electrode with a second pole, that the first and the second electrode comprise surfaces of the hip joint prosthesis, and in a state in which the end cap assembly closes the hollow space of the hip joint prosthesis, the coil assembly is predominantly arranged in the hollow space. For this purpose, the end cap is preferably provided with an inner volume in which the pick-up coil wound around an iron core is located. It is usefully glued into the end cap assembly. Here, the ends of the coil assembly suitably contact the electrically conductive surfaces forming tissue electrodes. Based upon the invention, the end cap thus obtains a double function. On the one hand, it prevents the ingrowth of connective tissue and bones into the prosthesis which could render a later explantation difficult. On the other hand, the end cap accommodates the components which give the hip joint prosthesis electrical properties. Aside from the mentioned advantages relating to the use of a hip joint prosthesis which—with respect to the mechanical properties—is largely unchanged as compared to the state of the art, it should further be noted that the surgeon may decide whether the prosthesis is to be closed using a conventional end cap or an end cap provided with electric components during the operation. Furthermore, the provision and storage of magnetically inducible end caps are substantially less complex and, thus, more cost effective than the provision of magnetically inducible hip joint prostheses with the requisite different dimensions. Other biological advantages are as follows: the risk of an infection is reduced by enhanced blood flow and immune response of the stimulated tissue, the antibiotic resistance of the multi-resistant staphylococcus aureus (MRSA) is overcome, and the adherence of bacteria films on the surface of the prosthesis body is avoided by the magnetically induced electric activation of the surface. In the extremely low-frequency non-thermal electromagnetic field flooding the entire hip joint region, an electric field which has been proved to be bactericidally effective in in vitro trials is induced on the surface of the joint prosthesis. This also applies to the dangerous adhesion of antibiotic resistant germs, for example, in the form of biofilms. This is avoided by the electrodynamic potential on the surface of the implant. Therefore, the joint prosthetic implant is also particularly suitable to act as what is commonly referred to as a "spacer" which is implanted in a two-step operation for sterilizing and regenerating the bone in case of infected hip joint replacements and may be replaced by an individual joint prosthesis after the development of an aseptic, load-bearing bone.

It is particularly preferred that a neck section proximally connected to the shaft-like section, carrying a femoral head and comprising at least a part of the hollow space is provided, wherein the hollow space permits the insertion of fixation means and of a tool for fixing the neck section to the shaft-like section, and that the end cap assembly proximally closes the hollow space of the neck section. The hollow space of the neck section thus obtains a double function. On the one hand, it enables the insertion of fixation means, in particular, a screw, and of a tool for fixing the neck section to the shaft-like section. On the other hand, it also offers sufficient space to fully or almost fully accommodate the end cap assembly inside the implant. The outer dimensions of the implant are kept small in this way, as the electrification does not require enlargement of the implant.

According to one variant, it is contemplated that the first electrode is formed by a contact surface of the end cap assembly and that the second electrode is formed by a contact surface of the shaft-like section. In this and other embodiments, the end cap assembly may be fully or partly formed of an insulating ceramic material, wherein an electrically conductive surface area may be realized by applying an electrically conductive material.

It is also possible that the first electrode is formed by a contact surface of the end cap assembly and that the second electrode is formed by a contact surface of the neck section. This arrangement of the electrodes is particularly useful if, for any reason, the propagation of the electric field in the area of the shaft-like section is to be avoided.

However, it is also possible and, in many situations, preferred that the first electrode is formed by a contact surface of the end cap assembly and that the second electrode is formed by a contact surface of the shaft-like section and of the neck section. If the neck section electrically contacts the shaft-like section, the entirety of shaft section and neck section may form one electrode, while the other electrode is formed by a surface of the end cap assembly.

It may further be contemplated that the first electrode is formed by a contact surface of the neck section, and that the second electrode is formed by a contact surface of the shaft-like section. Therefore, the end cap is not part of the electrode assembly, but instead, the electrodes are formed by the neck section and the shaft-like section.

According to a particularly preferred embodiment of the present invention, it is contemplated that the neck section is connected to the shaft-like section by means of an axially arranged, electrically insulating screw. In this way, the two sections of the implant, i.e., the shaft-like section and the neck section, may remain insulated from each other and form the pair of counter electrodes on this basis. For example, a zirconium oxide ($ZrO_2$) screw may be used.

In a further development of the invention, it is contemplated that a drug reservoir containing a drug is located in the hollow space and that the hollow space is connected to an outer section of the hip joint prosthesis via openings which enable a passage of the drug from the hollow space to the outer section.

According to a preferred embodiment, it is contemplated that the drug reservoir contains an antibiotic.

In this case, it has proved to be advantageous that the drug is flowable. In this way, the device according to the invention thus enables local antibiosis by activating thin antibiotics solutions on the surface of the implant and in the directly adjacent bone and soft tissue. This is particularly advantageous as antibiosis can be activated by the electromagnetic fields applied during the therapy.

The drug-related aspect of the invention can, for example, be implemented so that the drug reservoir is at least partly formed by a pressure-permeable container which at least partly releases its content when the hollow space is closed by the end cap assembly.

For example, it is possible that the end cap assembly carries the pressure-permeable container.

Prior to implantation, a ring-shaped tube filled with an antibiotic is introduced into the hollow space of the neck section or is carried by the end cap assembly, for example by being plugged into a tapered end of the end cap assembly. A thin antibiotic solution is located in the pressure permeable tube. The wall of the ring-shaped tube consists of a thin elastic plastic material which the solution can permeate under light pressure during insertion of the end cap, i.e., particularly when the end cap is screwed in.

It is also feasible that the drug reservoir cooperates with a controllable device, wherein the drug may be at least partly delivered by actuating the device. The drug, particularly the antibiotic, may, in this way, also be delivered in a targeted manner at any desired time. Thus, the delivery is not limited to that at the time of the implantation.

For example, it may be contemplated that the controllable device is suitable to directly or indirectly convert a magnetic impulse generated outside of the body into mechanical energy which effects delivery of the drug. A magnetic impulse may, for example, be converted into mechanical energy under the involvement of permanent magnetic or ferro-magnetic movable components so that the release of the drug is effected. Aside from this mechanical energy directly generated by the magnetic impulse, it is also possible that the magnetic impulse is detected by a device and then converted into a signal for generating mechanical energy of an actuator by circuit technology.

It is also feasible that the controllable device comprises an electric power storage, a receiver, an electric control circuit, and an actuator drivable by the electric control circuit so that the delivery of the drug can be effected by a signal generated outside of the body. The drivable actuator may, in particular, be a component of a drug pump.

It is particularly advantageous that the electric power storage is an accumulator chargeable with an electric voltage induced in the coil assembly. In this way, the variant comprising the electric power storage is also suitable for long-term-applications since the accumulator is chargeable at any time by means of a magnetic field applied from the outside which is deployed anyway within the course of the therapy, and which, in this respect, may provide the power for driving the drug pump.

The invention will now be described by way of example with reference to the accompanying drawings using preferred embodiments.

DETAILED DESCRIPTION OF THE DRAWINGS

In the following description of the drawings the same numerals designate the same or comparable components.

Figure 1:
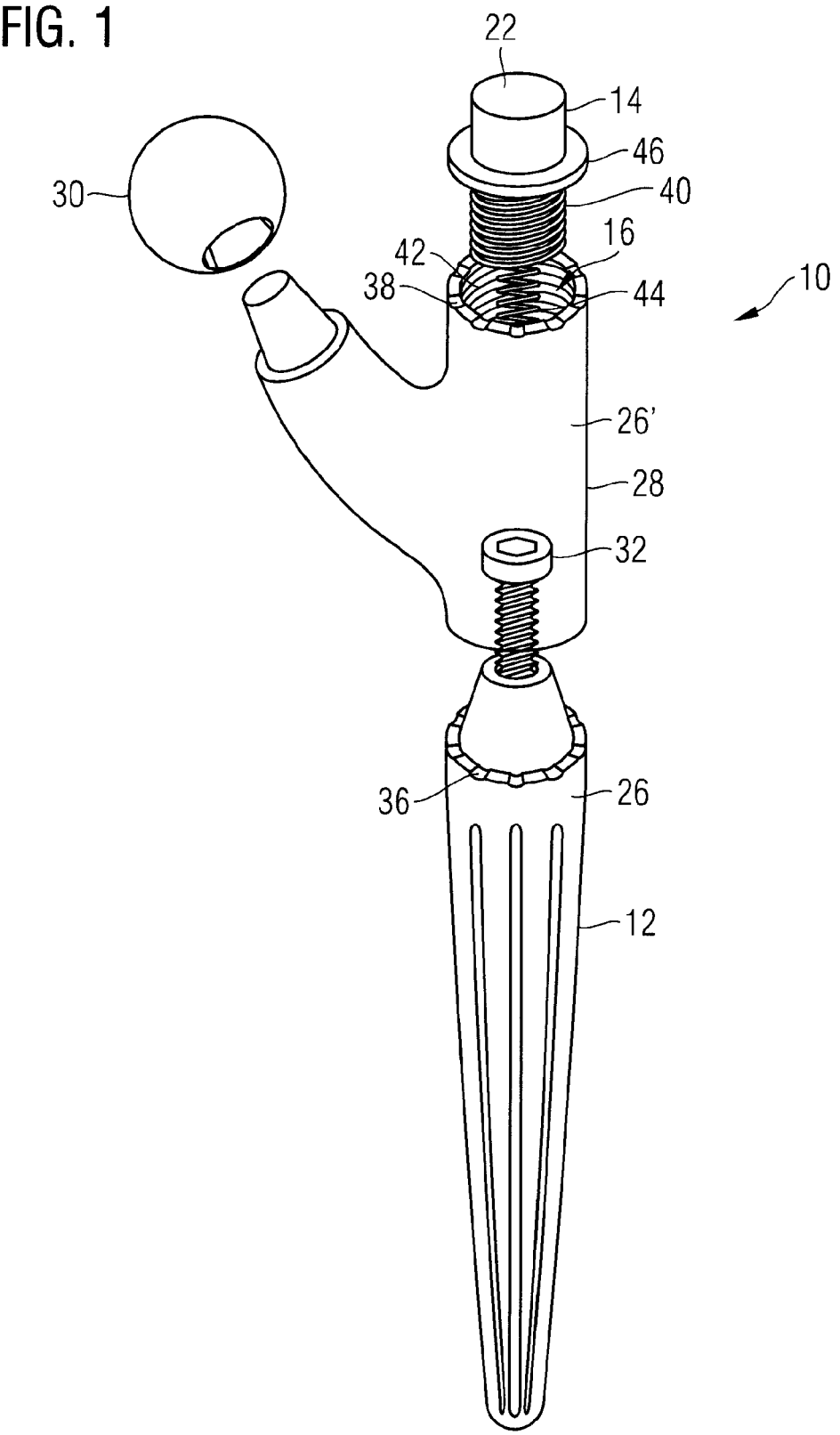
FIG. 1 shows a perspective exploded view of a hip joint prosthesis according to the invention.

FIG. 1 shows a perspective exploded view of a hip joint prosthesis 10 according to the invention. The hip joint prosthesis 10 comprises a shaft-like section 12, a neck section 28, a femoral head 30, and an end cap assembly 14. The neck section 28 is connectable to the shaft-like section 12 by means of a screw 32. The end cap assembly 14 comprises a male thread 40 which is screwable into a female thread 42 of the neck section 28. Inside the end cap assembly 14, electric components are arranged which will be described in more detail in connection with FIGS. 2 and 3. One pole of these electric components is electrically connected to a spring 44 carried by the end cap assembly 14. In the assembled state of the hip joint prosthesis 10, i.e., with the neck section 28 connected to the shaft-like section 12 by means of the screw 32 and the screwed-on end cap assembly 14 closing the hollow space 16, said spring 44 electrically contacts the axially arranged screw 32 directly or indirectly so that the shaft-like section 12 and/or the neck section 28 receive the electric potential of the spring 44. Therefore, the conductive surface sections of the shaft-like section 12 and/or the neck section will become electrodes 26, 26'. Another pole of the electric assembly is, for example, connected to a surface of the end cap assembly 14 so that the end cap 14 forms the counter electrode 22 to the electrode 26, 26' described above.

Figure 2:
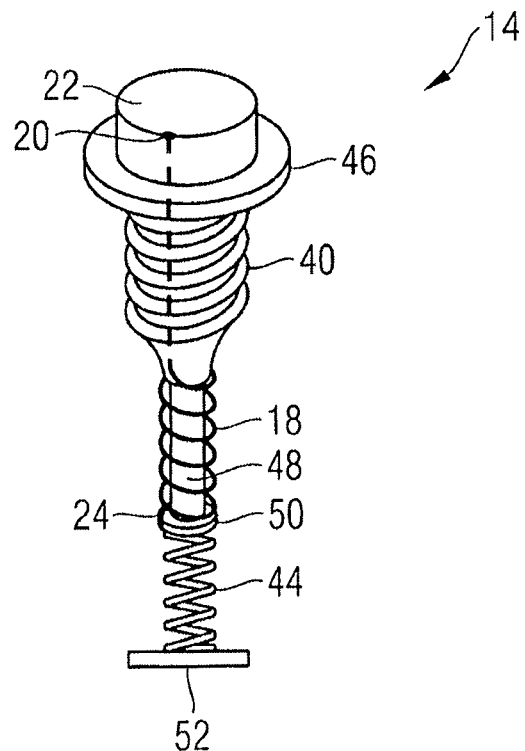
FIG. 2 shows a perspective exploded view of an end cap assembly of a hip joint prosthesis according to the invention.
Figure 3:
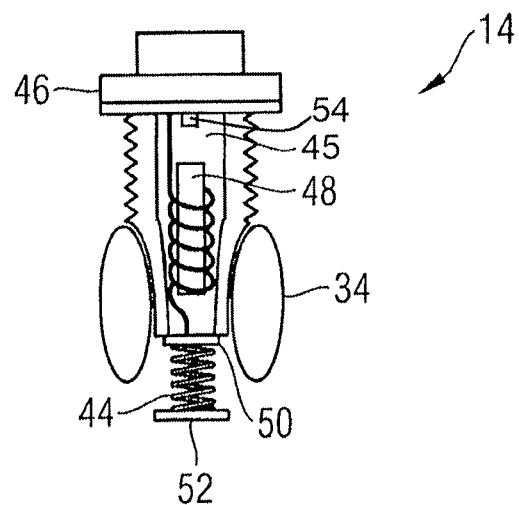
FIG. 3 shows an axial cross section of an end cap assembly of a hip joint prosthesis according to the invention.

FIG. 2 shows a perspective exploded view of an end cap assembly 14 of a hip joint prosthesis 10 according to the invention, and FIG. 3 shows an axial cross section of an end cap assembly 14 of a hip joint prosthesis 10 according to the invention. The end cap assembly 14 comprises a hollow space 45. A coil assembly 18 wound on an iron core 48 is insertable into the hollow space 45. After the insertion of the assembly into the hollow space 45, the assembly may be cemented into it, for example, using an epoxy resin adhesive, and the hollow space 45 may be distally closed by a panel 50, preferably by cementing the panel 50 to the threaded portion tapered in the distal direction. The metallic panel 50 electrically contacts a pole 24 of the coil assembly 18. The other pole 20 of the coil assembly 18 is connected to an electrically conductive surface 22 of the end cap assembly 14. The panel 50 is followed by the electrically conductive spring 44 already mentioned in connection with FIG. 1 in the distal direction, to which in turn an electrically conductive panel 52 is distally attached. If the end cap assembly 14 is inserted into the hip joint prosthesis, the panel 52 will establish an electric contact to the screw 32 (see FIG. 1). On this basis, different configurations of surface electrodes can be realized. For example, the body of the end cap assembly 14 carrying the thread 40 can be formed so as to be electrically insulating, preferably from aluminum oxide or zirconium oxide ceramics ($Al_2O_3$ or $ZrO_2$). A part of the surface the end cap assembly will then be transferred into an electrically conductive state, for example by sputtering or vaporizing an electrically conductive material. With the metallic panel 52 being connected to the screw 32 and, in turn, the screw 32 contacting the neck section 28 as well as the shaft-like section 12—both of which are manufactured from an electrically conductive metal—the neck section 28 and the shaft-like section 12 together form the counter electrode to the electrically conductive surface of the end cap assembly 14. It is also feasible to configure the screw 32 so as to be insulating and to ensure that no electric contact exists between the neck section 28 and the shaft-like section 12. Then, by establishing an electric contact, only the neck section 28 or parts of the neck section 28 may form the counter electrode to the end cap assembly 14. An electric contact between the distal pole of the coil assembly and the neck section 28 can also be avoided while an electric contact is established between this pole 24 and the shaft-like section. The electrically conductive surface of the end cap assembly 14 and the shaft-like section 12 then form counter electrodes without the involvement of the neck section 28. With a further embodiment, it is also possible that the end cap assembly 14 does not serve as an electrode. This may be realized in that the end cap assembly 14 is completely insulating on its surface, and the first pole 20 of the coil assembly 18 contacts the neck section 28 when the end cap assembly 14 is screwed into the neck section 28, for example, by a squeeze contact by means of the collar 46 of the end cap assembly.

FIG. 3 shows a useful embodiment of an end cap assembly 14 provided with another functionality. The end cap assembly 14 carries a drug reservoir 34. This drug reservoir is provided for local antibiosis in particular. The outer surface of the drug reservoir 34 is configured as a pressure-permeable wall so that a liquid drug solution can leak out when the end cap assembly 14 is screwed into the hollow space 16 (see FIG. 1) as the drug reservoir 34 is then compressed. Liquid leaking from the drug reservoir 34 may then leak from the hollow space 16 into the space outside of the hip joint prosthesis 10 through the openings 36, 38. Since it may also be useful not to have the drug solution leak into the neck section 28 as early as during the process of screwing in the end cap assembly 14, it may be contemplated that a controllable device 54, such as a drug pump which is directly or indirectly supplied with electric power by the coil assembly 18, is provided in the hollow space 16 of the neck section 28. For example, the coil assembly 18 may charge an accumulator which then provides the electric power required for the operation of the drug pump at any time. The operation of the drug pump may be controlled by a conventional transmitter-receiver device. It is also feasible to release the mechanic energy required for the timed discharge by a controllable device 54 responsive to a magnetic impulse.

The features of the invention disclosed in the above description, the drawings as well as the claims may be important for the realization of the invention individually as well as in any combination.

LIST OF REFERENCE NUMERALS 10 hip joint prosthesis
12 shaft-like section
14 end cap assembly
16 hollow space
18 coil assembly
20 first pole
22 first electrode
24 second pole
26 second electrode
28 neck section
30 femoral head
32 fixation means; electrically insulating screw
34 drug reservoir; pressure permeable container
36 opening
38 opening
40 male thread
42 female thread
44 electrically conductive spring
46 hollow space
48 iron core
50 panel
52 panel

The invention claimed is:
1. A hip joint prosthesis comprising:
a shaft section insertable into a femur; and
an end cap assembly closing a substantially closed hollow space of the hip joint prosthesis, the end cap assembly being in a proximal position relative to the femur when the hip joint prosthesis is in an implanted state, wherein:
the end cap assembly carries a coil assembly connected to a first electrode with a first pole and to a second electrode with a second pole;
the first and the second electrode comprise outer surfaces of the hip joint prosthesis; and
in a state in which the end cap assembly closes the hollow space of the hip joint prosthesis, the coil assembly is predominantly arranged in the hollow space.

2. The hip joint prosthesis according to claim 1, wherein:
a neck section is proximally connected to the shaft section, carrying a femoral head, and comprising at least a part of the hollow space is provided, the hollow space being configured to permit insertion of a device for fixing the neck section to the shaft section; and
the end cap assembly proximally closes the hollow space of the neck section.

3. The hip joint prosthesis according to claim 2, wherein:
the first electrode is formed by a contact surface of the end cap assembly; and
the second electrode is formed by a contact surface of the neck section.

4. The hip joint prosthesis according to claim 2, wherein:
the first electrode is formed by a contact surface of the end cap assembly; and
the second electrode is formed by a contact surface of the shaft section and of the neck section.

5. The hip joint prosthesis according to claim 2, wherein:
the first electrode is formed by a contact surface of the neck section; and
the second electrode is formed by a contact surface of the shaft section.

6. The hip joint prosthesis according to claim 5, wherein the neck section is connected to the shaft section by an axially arranged, electrically insulating screw.

7. The hip joint prosthesis according to claim 2, wherein:
the first electrode is formed by a contact surface of the end cap assembly; and
the second electrode is formed by a contact surface of the shaft section.

8. The hip joint prosthesis according to claim 2, wherein:
a drug reservoir containing a drug is located in the hollow space; and
the hollow space is connected to an outer section of the hip joint prosthesis via openings between the end cap assembly and the shaft section which enable a passage of the drug from the hollow space to the outer section when the end cap assembly is in an installed position closing the hollow space of the neck section.

9. The hip joint prosthesis according to claim 1, wherein:
the first electrode is formed by a contact surface of the end cap assembly; and
the second electrode is formed by a contact surface of the shaft section.

10. The hip joint prosthesis according to claim 1, wherein:
a drug reservoir containing a drug is located in the hollow space; and
the hollow space is connected to an outer section of the hip joint prosthesis via openings which enable a passage of the drug from the hollow space to the outer section.

11. The hip joint prosthesis according to claim 10, wherein the drug reservoir contains an antibiotic.

12. The hip joint prosthesis according to claim 10, wherein the drug is flowable.

13. The hip joint prosthesis according to claim 10, wherein the drug reservoir is at least partly formed by a pressure-permeable container which at least partly releases its content when the hollow space is closed by the end cap assembly.

14. The hip joint prosthesis according to claim 13, wherein the end cap assembly carries the pressure-permeable container.

15. The hip joint prosthesis according to claim 10, wherein the drug reservoir cooperates with a controllable device, wherein the drug may be at least partly released by actuating the device.

16. The hip joint prosthesis according to claim 15, wherein the controllable device is capable of directly or indirectly converting a magnetic impulse generated externally into mechanic energy effecting the release of the drug.

17. The hip joint prosthesis according to claim 15, wherein:
the controllable device comprises an electric power storage, a receiver, an electric control circuit, and an actuator drivable by the electric control circuit so that the release of the drug can be effected by an externally generated signal.

18. The hip joint prosthesis according to claim 17, wherein the electric power storage is an accumulator chargeable by an electric voltage induced in the coil assembly.

* * * * *